United States Patent [19]

Moore et al.

[11] 4,137,258

[45] Jan. 30, 1979

[54] PROCESS FOR MAKING PURE SALICYLIC ACID

[75] Inventors: Eugene R. Moore; Roger L. Briggs; David C. McDonald; Richard Hoffman, all of Midland, Mich.

[73] Assignee: The Dow Chemical Company, Midland, Mich.

[21] Appl. No.: 894,222

[22] Filed: Apr. 7, 1978

[51] Int. Cl.$^2$ ............................................. C07C 65/10
[52] U.S. Cl. ................................................... 562/477
[58] Field of Search ...................................... 260/521 B

[56] References Cited

U.S. PATENT DOCUMENTS

| 2,891,090 | 6/1959 | Campbell et al. | 260/521 B |
| 3,337,616 | 8/1967 | Kaeding | 260/521 B |
| 3,359,307 | 12/1967 | Poffenberger et al. | 260/521 B |
| 3,530,174 | 9/1970 | Gottesman | 260/521 B |

FOREIGN PATENT DOCUMENTS

| 208396 | 2/1955 | Australia | 260/521 B |
| 7143532 | 12/1971 | Japan | 260/521 B |
| 74006304 | 2/1974 | Japan | 260/521 B |
| 766887 | 1/1957 | United Kingdom | 260/521 B |
| 1201472 | 8/1970 | United Kingdom | 260/521 B |

OTHER PUBLICATIONS

Chem. Ber., 9:1212-1213, (1976).

*Primary Examiner*—Paul J. Killos
*Attorney, Agent, or Firm*—Ralph M. Mellom; Michael L. Glenn

[57] ABSTRACT

Alkali metal salicylate can be efficiently acidified and the salicylic acid product formed contemporaneously sublimed by contacting the salicylate as a solid with gaseous hydrogen chloride at the conditions specified. The temperature of the gaseous hydrogen chloride is controlled so that the heat required to sublime the salicylic acid product is predominantly supplied by the heat of reaction of the hydrogen chloride with the alkali metal salt of the carboxylic acid.

4 Claims, 1 Drawing Figure

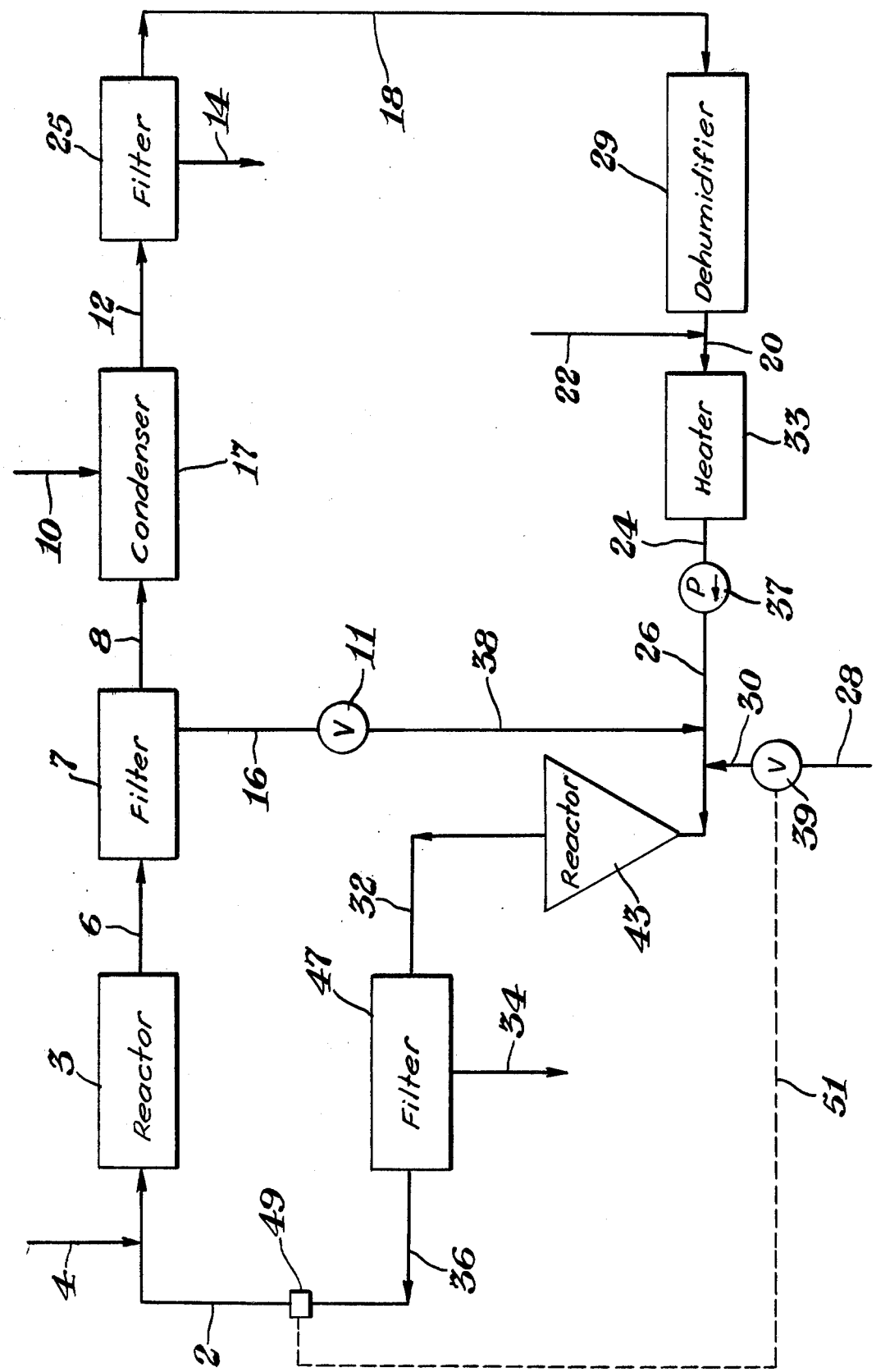

PROCESS FOR MAKING PURE SALICYLIC ACID

BACKGROUND OF THE INVENTION

This invention relates to the contemporaneous acidification of alkali metal salicylate and the sublimation of the salicyclic acid product.

It has long been known in the prior art that salicylic acid can be purified by sublimation. See, for example, U.S. Pat. Nos. 1,987,282 and 1,987,301. However, in the prior art the heat required to sublime the salicylic acid is supplied from external sources in a step separate and distinct from the acidification of the alkali metal salicylate.

Generally, the prior art acidifies sodium salicylate in a liquid medium containing a mineral acid to prepare salicylic acid. The liquid medium readily dissipates the heat of the acidification reaction. The salicylic acid is collected, dried and sublimed. The heat required to sublime the acid is imparted by a stream of heated gas or other means. The inefficiency of this heat transfer necessitates the use of relatively high temperatures which can decompose some of the salicylic acid.

In view of the deficiencies in the foregoing prior art methods of subliming salicylic acid, it would be highly desirable to provide a method of sublimation which utilizes the heat generated in the acidification of the alkali metal salicylate.

BRIEF DESCRIPTION OF THE DRAWING

The FIGURE is a schematic flow diagram illustrating a specific embodiment of a multistep process relating to the acidification of sodium salicylate and the sublimation of the salicylic acid product.

SUMMARY OF THE INVENTION

This invention is a method of making salicylic acid of high purity which comprises contacting an alkali metal salicylate in the solid phase with a gas stream containing gaseous, anhydrous hydrogen chloride so as to effect acidification to salicylic acid and contemporaneous sublimation of the salicylic acid to a gas.

Surprisingly, the practice of the present invention produces substantial acidification of alkali metal salicylate and employs the considerable heat produced by the acidification reaction to sublime the salicylic acid product. The fact that alkali metal salicylate can be introduced into the sublimation apparatus and acidified therein reduces the clogging of the inlet into the apparatus which occurs when salicyclic acid is introduced. Further, the sublimation of the salicylic acid contemporaneous with the acidification enhances the rapidity of acidification. Decomposition of the salicylic acid product can be reduced because the entering gas stream need not be at a temperature high enough to supply the heat required for sublimation.

DETAILED DESCRIPTION OF THE INVENTION

Alkali metal salicylate can be a sodium, potassium or operably, but less economically, a lithium salicylate. Impurities can be tolerated in the solid alkali metal salicylate as long as they do not interfere with the acidification reaction or sublimation of the salicylic acid product. For example, some alkali metal phenate, preferably no more than 1 percent by weight, can be present with the alkali metal salicylate to be acidified.

It is desirable, but not critical, that the alkali metal salicylate be finely divided to promote efficient acidification. A finely divided alkali metal salicylate is one having a surface area of at least about 1 square meter per gram, more advantageously at least about 2 square meters per gram, as determined by nitrogen adsorption analysis described in Johne, R. et al., Chem.-Ing.-Tech., 37:57-61 (1965). If the alkali metal salicylate is prepared in a manner which produces larger particles, it can be ground during or prior to acidification in any convenient way to a finely divided state.

The gas stream contacting the alkali metal salicylate with the exception of the hydrogen chloride component is advantageously inert to the reactants and products present in this reaction. Nitrogen and carbon dioxide are suitable components of the gas stream, but oxygen should be avoided because of the fire and explosive hazard the finely divided salicylic acid presents. The flow rate, temperature and hydrogen chloride content of the gas stream should be controlled to prevent saturation of the gas stream with vaporized salicylic acid which can result in premature condensation of the salicylic acid.

The alkali metal salicylate can conveniently be brought together with a stoichiometric amount or slight excess of hydrogen chloride in the gas stream over a period of time to effect substantial acidification with minimal waste of hydrogen chloride. Any hydrogen chloride remaining in the gas stream after acidification is desirably removed by a scrubber or in some other manner known to the art.

The manner in which the gas stream contacts the solid phase alkali metal salicylate is not necessarily critical to the practice of this invention. The gas stream can flow over or pass through a bed of finely divided alkali metal salicylate or contact it in any convenient manner so as to effect intimate contact between the hydrogen chloride gas and the alkali metal salicylate. A solids mixer can also be used during acidification to advantage to enhance reaction rate and product sublimation. Advantageously, the solid phase alkali metal salicylate can be entrained in the gas stream to effect intimate contact between the gas and the solid.

The temperature of the gas stream in order to effect contemporaneous sublimation of the salicyclic acid product should be in the range from about 90° C. to about 200° C., preferably from about 90° C. to about 170° C. Lower temperatures than the foregoing preferred ranges are operable, but the gas stream at these temperatures carries too small an amount of the vaporized salicylic acid to be practical. Higher temperatures than the foregoing preferred ranges, while operable, produce undesirable decomposition of the salicylic acid. Advantageously, the sodium salicylate is maintained at a temperature below its softening point to prevent fusing the salicylate which reduces its surface area. The term contemporaneous sublimation as used in this application indicates that the heat required to sublime the acid product is predominantly supplied by the heat of reaction of hydrogen chloride with the alkali metal salicylate.

The salicylic acid vapor contained in the gas stream after sublimation can be collected by cooling the gas in any convenient manner to condense the salicylic acid, for example with a water spray. U.S. Pat. No. 2,448,868 is of interest in that it teaches the condensation of gaseous phthalic anhydride with a water spray. The gas stream is advantageously filtered or otherwise treated as with a cyclone separator prior to cooling to remove any solids entrained in the gas. If the gas stream is properly filtered the salicylic acid collected is substantially free of alkali metal salicylate and alkali metal chloride.

The embodiment of this invention wherein the sodium salicylate is acidified and the acid product contemporaneously sublimed can be practiced in a variety of apparatus and process steps as will be understood from the foregoing description. The FIGURE is a schematic drawing illustrating a preferred embodiment.

In the preferred embodiment depicted in the FIGURE a continuous, two-step acidification process is employed. Various items of equipment, such as valve fittings and the like, are omitted from the drawing so as to simplify the description of the invention. However, those skilled in the art will realize that such conventional equipment can be employed as desired.

In the embodiment depicted in the FIGURE, finely divided sodium salicylate is countercurrently introduced through conduit 4 into a stream of gas flowing through conduit 2. The gas stream consists predominantly of a gas inert to the reactants, such as nitrogen or carbon dioxide, and contains gaseous hydrogen chloride and gaseous salicylic acid. The temperature of the stream of inert gas is controlled by heater 33 to prevent condensation of the salicylic acid without softening the sodium salicylate, preferably being in the range from about 90° C. to about 180° C., more preferably from about 130° C. to about 170° C. The sodium salicylate introduced into the gas stream is preferably heated to prevent excessive cooling of the gas stream and premature condensation of salicylic acid. A sufficient mole excess of sodium salicylate is introduced, so that the hydrogen chloride in the gas stream will be substantially exhausted in reaction with the sodium salicylate. The gas stream containing the entrained sodium salicylate is conducted through conduit 2 into reactor 3. The excess sodium salicylate reacts in reactor 3 with the hydrogen chloride present in the gas stream to substantially eliminate the hydrogen chloride. To prevent the entrained salicylate from settling out, the reactor 3 is advantageously a relatively small diameter, tall vessel in which conduit 2 discharges at the top.

The entrained sodium chloride by-product of the acidification and the entrained remaining amount of sodium salicylate are forwarded from reactor 3 through conduit 6 into filter 7. In filter 7 the entrained solids are separated from the gas stream and shunted into conduit 16. The gas stream passes through the filter into conduit 8. Conveniently, filter 7 can be a simple bag filter made from a heat resistant filtering material. Such a bag filter can be periodically cleaned of collected solids with a pulse of inert gas in the reverse direction of the gas stream flow.

The inert gas stream containing the salicylic acid vapor is forwarded through conduit 8 into a condenser 17 where the temperature of the stream is cooled to a temperature at which the salicylic acid condenses. A fine water mist is introduced into condenser 17 through conduit 10. The introduction of the water into the condenser 17 should be controlled so as to effect transfer of heat contained in the gas stream into evaporation of the water without condensation.

The gas stream containing the condensed salicylic acid is forwarded from the condenser 17 to the filter 25 through the conduit 12. The filter 25 separates the salicylic acid from the gas stream and forwards it into exit conduit 14. The filter 25 can be any device known in the art to readily separate gases from solids such as a cyclone separator or a bag filter. The solid-free gas stream is forwarded from the filter through conduit 18 into the dehumidifier 29 wherein a substantial portion of the water introduced by condenser 17 is removed.

The dehumidified gas stream is forwarded from dehumidifier 29 to the heater 33 through conduit 20. Heater 33 elevates the gas stream's temperature to a degree suitable for the acidification-sublimation step. Conduit 22 introduces whatever additional volume of gas is required into conduit 20. The heated gas stream is forwarded from heater 33 to pump 37 through conduit 24. Pump 37 supplied the force which drives the gas stream at the velocity required to prevent the entrained solids from settling from the gas stream prior to the filtering steps.

The gas stream is conducted from pump 37 to reactor 43 through conduit 26. The solids removed in filter 7 are introduced into conduit 16, pass through gas-tight valve 11 into conduit 38 and then are introduced into conduit 26. The solids introduced through conduit 38 are entrained in the gas stream in conduit 26 and carried into reactor 43.

Hydrogen chloride gas passes through conduit 28 into valve 39 and then is introduced into conduit 26 through conduit 30. The hydrogen chloride introduced into the gas stream in conduit 26 is controlled to maintain an excess relative to the sodium salicylate present.

Reactor 43 is designed so that only the gas stream and very finely divided particles entrained in the gas stream can exit through conduit 32. Conveniently, an inverted cone shape is employed in reactor 43, such that the velocity of the gas stream suffices to fluidize the reactants in the reactor and forward only the fine sodium chloride particles and not the larger sodium salicylate particles through conduit 32 into filter 47. Of course, the vaporized salicylic acid product enters the gas stream.

Filter 47 separates the solids, predominantly sodium chloride, from the gas stream and forwards the solids into exit conduit 34. The gas stream is forwarded from the filter 47 to a chloride analyzer 49 by the conduit 36. The chloride analyzer 49 periodically monitors the total chloride in the gas stream. This chloride measurement can be passed through a control system 51 to adjust valve 39 to maintain the hydrogen chloride excess in the range from about 30 to about 80 mole percent. The control system can be any human or machine agency well-known in the art.

The gas stream exits from chloride analyzer 49 into conduit 2. This gas stream in conduit 2 contains hydrogen chloride and salicylic acid gas as well as the inert gas. Sodium salicylate is introduced into the gas stream through conduit 4 in the first stage previously described.

The pressure of the system in the preferred embodiment described immediately above is advantageously at or near atmospheric pressure. As the pressure is increased above ten atmospheres the process becomes impractical due to the relatively large mass of gas that must be cooled to dehumidify the gas and then reheated to yield a given amount of salicylic acid. As the pressure is reduced to subatmospheric pressures, the concentration of salicylic acid in the gas stream increases, reducing the energy necessary to cool and reheat the gas. However, specialized equipment is necessary to operate at negative pressures.

Time of reaction in the preferred embodiment is difficult to measure, but residence time of sodium salicylate in the system calculated from gas flow rates is typically less than ten minutes on average. As particle surface area is decreased below 2 square meters per gram, somewhat longer residence times are required. Residence times would also be relatively longer at lower temperatures in the preferred range and shorter at higher temperatures.

It is possible to operate the preferred embodiment over a wide range of conversions of sodium salicylate to salicylic acid, but it is advantageous to operate at greater than about 80 mole percent conversion, more advantageously greater than about 95 mole percent conversion. In an operable, but less desirable embodiment, an overall mole excess of hydrogen chloride can be employed relative to the sodium salicylate present in the system to effect substantially complete acidification, but the excess acid will pass through the reactor 3 into the spray chamber condenser 17 where it is not desired. Furthermore, the incremental improvement in the degree of conversion diminishes as the excess of hydrogen chloride gas increases. Thus, after the start-up period for the system in which an excess of sodium salicylate is introduced, desirably equimolar amounts of hydrogen chloride and sodium salicylate are introduced into the gas stream over a period of time. Advantageously, to promote ease in control, the hydrogen chloride and sodium salicylate are introduced into the gas stream at substantially constant rates during the acidification.

Procedures in Examples

The specific examples that follow illustrate the invention, but are not to be taken as limiting its scope.

EXAMPLE 1

In the manner depicted in the figure, sodium salicylate prepared from sodium phenate by the Kolbe-Schmitt reaction is acidified and the acid product spontaneously sublimed. Sodium salicylate at a temperature of about 110° C. is introduced by conduit 4 into a gas stream consisting of nitrogen, hydrogen chloride and, after start-up, salicylic acid, maintained by heater 33 at 168° C. The hydrogen chloride is completely reacted with the sodium salicylate in reactor 3. As the hydrogen chloride content of the gas stream is not constant, from about 30 to about 80 mole percent of the sodium salicylate in reactor 3 is converted to acid at various times. The average residence time of the gas stream in reactor 3 is about 15 seconds.

Condenser 17 reduces the temperature of the gas stream from about 160° C. to about 80° C. after the solids are removed in filter 7. The gas stream is cooled to about 40° C. in the dehumidifier after the condensed salicylic acid is removed by filter 25. Heater 33 elevates the temperature of the gas stream to 174° C. and pump 37 recirculates the gas. The gas stream passes through the remaining stages depicted in FIG. 1.

After about 43 hours the reaction is terminated. During the course of the reaction about 580 kilograms (3560 gram moles excluding impurities) of crude sodium salicylate containing about 10 kilograms of impurities are introduced into the reactor. During the reaction about 147 kilograms (3900 gram moles) of hydrogen chloride are added to the reaction. About 409 kilograms (2960 gram moles) of salicylic acid product is collected by the salicylic acid filter for an isolated yield of 83 mole percent based on the sodium salicylate. Only about 37 kilograms (270 gram moles) of the salicylic acid, which is only about 7.6 mole percent of the theoretical yield based on the sodium salicylate, is lost as an impurity in the sodium chloride.

EXAMPLE 2

In a series of separate acidifications carried on in a manner similar to Example 1, the mole ratio of hydrogen chloride to sodium salicylate introduced into the gas stream is varied from one acidification to another. The sodium chloride collected by the salt filter is then analyzed to determine the sodium salicylate present in the salt as a mole percentage of the sodium salicylate introduced into the gas stream for acidification. The hydrogen chloride introduced into the gas stream as a mole percentage of the moles of sodium salicylate introduced is tabulated in Table I, as is the mole percentage of sodium salicylate present in the sodium chloride.

TABLE I

| HCl Percentage of Theoretical | Percentage Salicylate in Salt |
|---|---|
| 88.0 | 24.0 |
| 89.0 | 15.5 |
| 92.0 | 9.8 |
| 93.5 | 3.8 |
| 94.0 | 7.2 |
| 94.5 | 3.3 |
| 95.0 | 3.8 |
| 97.0 | 4.2 |
| 97.0 | 4.7 |
| 97.5 | 7.0 |
| 99.0 | 4.0 |
| 99.5 | 4.7 |
| 103.0 | 3.0 |
| 106.0 | 3.4 |
| 110.0 | 3.7 |
| 111.0 | 3.8 |
| 147.0 | 2.3 |

A pattern of a decreasing percentage of the sodium salicylate in the sodium chloride with increasing percentages of hydrogen chloride emerges from the tabulated data. However, as the amount of hydrogen chloride approaches the stoichiometric amount the incremental decline in the percent salicylate lost in the salt approaches zero. This relationship indicates that it is preferable that the mole percent of hydrogen chloride introduced is preferably in the range from about 90 to about 110 percent, more preferably from about 95 to about 105 percent and most preferably from about 98 to 102 percent of the stoichiometric number of moles.

EXAMPLE 3

In a manner similar to Example 1, sodium salicylate is introduced into a gas stream consisting of nitrogen, hydrogen chloride and, after start-up, salicylic acid. The dehumidified gas is heated to a temperature of 175° C. in the heater and the gas stream still retains a temperature of 166° C. immediately before it is cooled in the spray condenser. Sodium salicylate can be introduced into the reactor in the above manner at a rate of 32 pounds of sodium salicylate per hour without saturating the gas stream with salicylic acid.

In a comparative example not embodying this invention, but representative of prior art techniques, salicylic acid is sublimed to purify it. Salicylic acid with an amount of sodium chloride equal to that produced in embodiments of the claimed method is introduced into a nitrogen stream heated to a temperature of 237° C. Even at a gas stream flow rate greater than that in the embodiments of the claimed method, salicylic acid must be introduced into this system at a rate of less than 20 pounds per hour to prevent saturation of the gas stream with salicylic acid. Even at the high temperature and gas flow employed herein, the heat required to sublime the salicylic acid is such that the temperature of the gas declines to 156° C. during substantially complete sublimation.

A comparison of the methods depicted immediately above demonstrates that the claimed method uses less energy by requiring less gas at a lower temperature than the prior art method. The claimed method also permits increased rates of sublimation. Further, less decomposition of the salicylic acid occurs in the claimed method because of the relatively lower maximum temperature employed.

What is claimed is:

1. A method of making salicylic acid of high purity comprising contacting sodium salicylate in the solid phase with a gas stream containing gaseous anhydrous hydrogen chloride so as to effect acidification of salicylic acid and contemporaneous sublimation of salicylic acid to a gas.

2. The method as defined in claim 1 wherein the gas stream is maintained at a temperature in the range from about 90° C. to about 200° C.

3. A method of making salicyclic acid of high purity from sodium salicylate in a continuous, two-step acidification process comprising the steps of:
 (a) in the first step, sodium salicylate in the solid phase is contacted at a reaction temperature below its softening point with a gas stream containing a greater than stoichiometric amount of gaseous, anhydrous hydrogen chloride to effect substantially complete acidification and the salicylic acid product is contemporaneously sublimed into the gas stream;
 (b) in the second step, the gas stream contacts a greater than stoichiometric amount of sodium salicylate in the solid phase at reactive conditions so as to effect acidification to the substantially complete exhaustion of the hydrogen chloride remaining in the gas stream, the salicylic acid product is contemporaneously sublimed and the unreacted sodium salicylate is cycled back to the first step.

4. The method as defined in claim 3 wherein the sublimed salicylic acid product is condensed to a solid by means of a fine water spray controlled so as to effect transfer of heat contained in the gas stream into evaporation of the water without condensation.